(12) United States Patent
Couture

(10) Patent No.: US 11,813,180 B2
(45) Date of Patent: Nov. 14, 2023

(54) RANGE OF MOTION EVALUATION IN ORTHOPEDIC SURGERY

(71) Applicant: Exactech, Inc., Gainesville, FL (US)

(72) Inventor: Pierre Couture, Montreal (CA)

(73) Assignee: Exactech, Inc., Gainesville, FL (US)

( * ) Notice: Subject to any disclaimer, the term of this patent is extended or adjusted under 35 U.S.C. 154(b) by 42 days.

(21) Appl. No.: 17/345,947

(22) Filed: Jun. 11, 2021

(65) Prior Publication Data

US 2022/0133506 A1    May 5, 2022

Related U.S. Application Data

(63) Continuation of application No. 16/262,482, filed on Jan. 30, 2019, now abandoned.
(Continued)

(51) Int. Cl.
*A61F 2/46* (2006.01)
*A61B 34/30* (2016.01)
(Continued)

(52) U.S. Cl.
CPC ............ *A61F 2/4657* (2013.01); *A61B 34/30* (2016.02); *A61F 2/4607* (2013.01); *A61F 2/4684* (2013.01); *A61B 2034/102* (2016.02); *A61B 2034/105* (2016.02); *A61B 2034/108* (2016.02); *A61B 2034/2048* (2016.02); *A61B 2034/2055* (2016.02); *A61B 2034/252* (2016.02);
(Continued)

(58) Field of Classification Search
CPC ...... A61F 2/461; A61F 2/4684; A61F 2/4627; A61F 2002/467; A61F 2002/4633; A61B 34/30; A61B 2034/108; A61B 2034/2048; A61B 2090/065; A61B 2034/105; A61B 2034/2055; A61B 2034/252; A61B 2090/061
See application file for complete search history.

(56) References Cited

U.S. PATENT DOCUMENTS

| | | |
|---|---|---|
| 4,501,266 A | 2/1985 | McDaniel |
| 5,470,354 A | 11/1995 | Hershberger et al. |

(Continued)

FOREIGN PATENT DOCUMENTS

| | | |
|---|---|---|
| AU | 2019214335 A1 | 7/2020 |
| CN | 1810208 A | 8/2006 |

(Continued)

OTHER PUBLICATIONS

"U.S. Appl. No. 16/262,465, Non Final Office Action dated Dec. 16, 2020", 8 pgs.

(Continued)

*Primary Examiner* — Anu Ramana
(74) *Attorney, Agent, or Firm* — GREENBERG TRAURIG, LLP

(57) ABSTRACT

A system and method may be used to evaluate soft tissue. A hip joint evaluation may use an adjustable spacer, such as varying sized physical spacers or an inflatable bladder, along with a sensor to measure force, pressure, gap distance, or the like, for example during a range of motion test. A method may include using a maximum pressure during the range of motion test to determine a maximum pressure during the range of motion test. The maximum pressure may be output for display on a user interface.

18 Claims, 7 Drawing Sheets

Related U.S. Application Data

(60) Provisional application No. 62/697,227, filed on Jul. 12, 2018, provisional application No. 62/697,220, filed on Jul. 12, 2018, provisional application No. 62/625,706, filed on Feb. 2, 2018.

(51) Int. Cl.
   *A61B 34/10* (2016.01)
   *A61B 34/20* (2016.01)
   *A61B 90/00* (2016.01)
   *A61B 34/00* (2016.01)

(52) U.S. Cl.
   CPC ... *A61B 2090/064* (2016.02); *A61F 2002/467* (2013.01); *A61F 2002/4633* (2013.01)

(56) References Cited

U.S. PATENT DOCUMENTS

| | | | |
|---|---|---|---|
| 5,682,886 A * | 11/1997 | Delp | A61B 90/36 |
| | | | 600/407 |
| 5,733,292 A | 3/1998 | Gustilo et al. | |
| 6,859,661 B2 | 2/2005 | Tuke | |
| 7,604,637 B2 | 10/2009 | Johnson et al. | |
| 7,819,881 B2 | 10/2010 | Stone et al. | |
| 8,337,508 B2 | 12/2012 | Lavallee et al. | |
| 8,480,754 B2 * | 7/2013 | Bojarski | A61F 2/5046 |
| | | | 623/20.14 |
| 8,652,148 B2 | 2/2014 | Zuhars | |
| 8,656,790 B2 | 2/2014 | Amirouche | |
| 8,814,877 B2 * | 8/2014 | Wasielewski | A61B 17/00 |
| | | | 606/91 |
| 9,259,278 B2 | 2/2016 | Jensen | |
| 9,364,294 B2 | 6/2016 | Razzaque et al. | |
| 9,433,471 B2 | 9/2016 | Zuhars | |
| 9,572,588 B2 | 2/2017 | Fisher et al. | |
| 9,808,356 B2 | 11/2017 | Haight et al. | |
| 10,136,951 B2 | 11/2018 | Razzaque et al. | |
| 10,136,952 B2 | 11/2018 | Couture et al. | |
| 10,154,836 B2 * | 12/2018 | D'Lima | A61B 17/025 |
| 10,194,991 B2 | 2/2019 | Bonny et al. | |
| 10,206,791 B2 * | 2/2019 | D'Lima | A61B 17/1764 |
| 10,456,263 B2 | 10/2019 | Bojarski et al. | |
| 11,173,049 B2 * | 11/2021 | D'Lima | A61F 2/4657 |
| 2002/0052606 A1 * | 5/2002 | Bonutti | A61B 17/0401 |
| | | | 606/88 |
| 2004/0236424 A1 | 11/2004 | Berez et al. | |
| 2004/0243148 A1 | 12/2004 | Wasielewski | |
| 2004/0254771 A1 * | 12/2004 | Riener | G09B 23/32 |
| | | | 703/7 |
| 2005/0027226 A1 | 2/2005 | Stutz et al. | |
| 2005/0251148 A1 | 11/2005 | Friedrich et al. | |
| 2006/0241569 A1 * | 10/2006 | DiSilvestro | A61F 2/461 |
| | | | 606/1 |
| 2007/0198022 A1 | 8/2007 | Lang et al. | |
| 2007/0219561 A1 | 9/2007 | Lavallee et al. | |
| 2007/0234819 A1 | 10/2007 | Amirouche et al. | |
| 2007/0244488 A1 | 10/2007 | Metzger et al. | |
| 2009/0018544 A1 | 1/2009 | Heavener | |
| 2009/0299228 A1 | 12/2009 | Lozier et al. | |
| 2010/0249658 A1 | 9/2010 | Sherman | |
| 2010/0249787 A1 | 9/2010 | Roche | |
| 2010/0249791 A1 | 9/2010 | Roche | |
| 2011/0029093 A1 | 2/2011 | Bojarski | |
| 2012/0158152 A1 | 6/2012 | Claypool et al. | |
| 2013/0013076 A1 | 1/2013 | Fisher et al. | |
| 2013/0197542 A1 | 8/2013 | Bonutti | |
| 2013/0211531 A1 | 8/2013 | Steines et al. | |
| 2013/0261505 A1 | 10/2013 | Sherman | |
| 2013/0267959 A1 | 10/2013 | Engh et al. | |
| 2013/0317344 A1 | 11/2013 | Borus et al. | |
| 2013/0331850 A1 | 12/2013 | Bojarski et al. | |
| 2015/0057758 A1 | 2/2015 | Axelson, Jr. et al. | |
| 2015/0105782 A1 | 4/2015 | D'lima et al. | |
| 2015/0106024 A1 * | 4/2015 | Lightcap | A61B 5/4851 |
| | | | 600/587 |
| 2016/0278754 A1 | 9/2016 | Todorov et al. | |
| 2016/0278944 A1 | 9/2016 | D'lima et al. | |
| 2017/0360512 A1 | 12/2017 | Couture et al. | |
| 2019/0053859 A1 | 2/2019 | Couture et al. | |
| 2019/0167447 A1 | 6/2019 | Angibaud | |
| 2019/0240045 A1 | 8/2019 | Couture | |
| 2019/0240046 A1 | 8/2019 | Couture | |
| 2022/0133505 A1 | 5/2022 | Couture | |

FOREIGN PATENT DOCUMENTS

| | | |
|---|---|---|
| CN | 103957992 A | 7/2014 |
| CN | 105682612 A | 6/2016 |
| CN | 107530097 A | 1/2018 |
| CN | 111615359 A | 9/2020 |
| CN | 111629685 A | 9/2020 |
| EP | 1226788 A1 | 7/2002 |
| WO | 03/079940 A2 | 10/2003 |
| WO | 2009/046547 A1 | 4/2009 |
| WO | WO-2009046547 A1 | 4/2009 |
| WO | 2010/015877 A1 | 2/2010 |
| WO | WO-2010015877 A1 | 2/2010 |
| WO | 2014/144107 A1 | 9/2014 |
| WO | WO-2014144107 A1 | 9/2014 |
| WO | WO-2014149079 A1 | 9/2014 |
| WO | 2017/178951 A1 | 10/2017 |
| WO | WO-2017178951 A1 | 10/2017 |
| WO | WO-2019148284 A1 | 8/2019 |

OTHER PUBLICATIONS

"U.S. Appl. No. 16/262,465, Response filed Sep. 16, 2020 to Restriction Requirement dated Jul. 22, 2020", 7 pgs.

"U.S. Appl. No. 16/262,465, Restriction Requirement dated Jul. 22, 2020", 5 pgs.

"U.S. Appl. No. 16/262,482, Non Final Office Action dated Dec. 16, 2020", 8 pgs.

"U.S. Appl. No. 16/262,482, Response filed Sep. 16, 2020 to Restriction Requirement dated Jul. 23, 2020", 7 pgs.

"U.S. Appl. No. 16/262,482, Restriction Requirement dated Jul. 23, 2020", 5 pgs.

"Australian Application Serial No. 2019214335, First Examination Report dated Jan. 20, 2021", 4 pgs.

"Australian Application Serial No. 2019214338, First Examination Report dated May 21, 2021", 3 pgs.

"International Application Serial No. PCT/CA2019/050119, International Preliminary Report on Patentability dated Aug. 13, 2020", 6 pgs.

"International Application Serial No. PCT/CA2019/050119, International Search Report dated Apr. 18, 2019", 3 pgs.

"International Application Serial No. PCT/CA2019/050119, Written Opinion dated Apr. 18, 2019", 4 pgs.

"International Application Serial No. PCT/CA2019/050124, International Search Report dated Apr. 26, 2019", 9 pgs.

"International Application Serial No. PCT/CA2019/050124, Written Opinion dated Apr. 26, 2019", 6 pgs.

"Traditional 510(k) Premarket Notification XO Knee Balancing System", XpandOrtho, Inc., (Aug. 3, 2016), 1278 pgs.

"XpandOrtho XO Knee Balancing System", XpandOrtho, (Mar. 31, 2017), 13 pgs.

Bhandari, Mohit, et al., "Ligament balancing in total knee arthroplasty", JointEvidence; Lit. No. 1898-e, (Mar. 2009), 44 pgs.

Collo, A., et al., "An Active Tibial Component for Postoperative Fine-Tuning Adjustment of Knee Ligament Imbalance", 2014 5th IEEE RAS & EMBS International Conference on Biomedical Robotics and Biomechatronics (BioRob), (Aug. 2014), pp. 126-131.

Colwell Jr., Clifford W., et al., "Self-Adapting Electronic Intraoperative Ligament Balance Predicts Postoperative Knee Kinematics", ORS 2016 Annual Meeting Poster No. 1876, Shiley Center for Orthopaedic Research & Education, (Mar. 2016), 1 pg.

Colwell, Jr., C.W., et al., "The Electronic Knee", Total Knee Arthroplasty; Chapter 45, (2005), pp. 282-287.

(56) References Cited

OTHER PUBLICATIONS

D'Lima, Daryl D., et al., "Dynamic Intraoperative Ligament Balancing for Total Knee Arthroplasty", Clinical Orthopaedics and Related Research; No. 463, (Jul. 2007), pp. 208-212.

D'Lima, D., et al., "Novel Electronic Intraoperative Ligament Balance Predicts Postoperative Knee Kinematics", Orthopaedic Proceedings vol. 98-B, No. Supp 7, (Feb. 21, 2018), 3 pgs.

D'Lima, Darryl D., et al., "Intraoperative Measurements and Tools to Assess Stability", Journal of the American Academy of Orthopaedic Surgeons, vol. 25, Supplement 1, (Feb. 2017), pp. S29-S32.

D'Lima, Darryl, et al., "The Science of Knee Ligament Balance", Orthopaedic Proceedings vol. 98-B, No. Supp 1, (Feb. 21, 2018), 3 pgs.

Fregly, Benjamin J., et al., "Grand Challenge Competition to Predict In Vivo Knee Loads", Journal of Orthopaedic Research, (Apr. 2012), pp. 503-513.

Gerus, Pauline, et al., "Subject-specific knee joint geometry improves predictions of medial tibiofemoral contact forces", J Biomech.; 46(16), (Nov. 15, 2013), 19 pgs.

Gustke, K.A., et al., "Increased satisfaction after total knee replacement using sensor-guided technology", Bone Joint J; 96-B: No. 10, (Oct. 2014), pp. 1333-1338.

Kirking, Bryan, et al., "A multiaxial force-sensing implantable tibial prosthesis", Journal of Biomechanics, vol. 39, Issue 9; https://doi.org/10.1016/j.jbiomech.2005.05.023, (2006), 2 pgs.

Kwak, Dai-Soon, et al., "Development of a Pneumatic Tensioning Device for Gap Measurement during Total Knee Arthroplasty", Clinics in Orthopedic Surgery;4:1, (Sep. 2012), pp. 188-192.

Marmignon, C., et al., "Automated hydraulic tensor for Total Knee Arthroplasty", Int J Medical Robotics and Computer Assisted Surgery 2005;1(4); (www.bjs.co.uk), (Oct. 2005), pp. 51-57.

Nagamine, Ryuji, et al. "Comparison of Values of Joint Gap Distance and Angle After Each Step of Medial Soft-Tissue Release Between Offset and Standard Tensor/Balancers in TKA", Orthopaedic Proceedings vol. 98-B, No. Supp 3, (Feb. 21, 2018), 3 pgs.

Nielsen, Evan S., et al., "Second-Generation Electronic Ligament Balancing for Knee Arthroplasty: A Cadaver Study", The Journal of Arthroplasty 33, (Fe. 2018), pp. 2293-2300.

Wium, Daniël Jacobus, "Development of a dynamic tensioner device for joint gap stiffness during knee arthroplasty", Stellenbosch University https://scholar.sun.ac.za, (Mar. 2018), 145 pgs.

Zhao, Dong, et al., "In Vivo Medial and Lateral Tibial Loads during Dynamic and High Flexion Activites", Journal of Orthopaedic Research, (May 2007), pp. 593-602.

"U.S. Appl. No. 17/345,918, Preliminary Amendment filed Mar. 2, 2022", 6 pgs.

"Australian Application Serial No. 2019214338, Response filed Apr. 28, 2022 to First Examination Report dated May 21, 2021", 12 pgs.

"Australian Application Serial No. 2019214338, Subsequent Examiners Report dated May 3, 2022", 4 pgs.

"Canadian Application Serial No. 3,088,912, Examiner's Rule 86(2) Requisition dated Jul. 14, 2022", 4 pgs.

"Canadian Application Serial No. 3,089,218, Examiner's Rule 86(2) Requisition dated Mar. 30, 2022", 3 pgs.

"European Application Serial No. 19747526.2, Response filed May 9, 2022 to Extended European Search Report dated Oct. 11, 2021", 21 pgs.

"European Application Serial No. 19747760.7, Response filed May 11, 2022 to Extended European Search Report dated Oct. 21, 2021", 23 pgs.

U.S. Appl. No. 17/345,918, filed Jun. 11, 2021, Soft Tissue Balancing in Robotic Knee Surgery.

"Australian Application Serial No. 2019214335, Response filed Jan. 4, 2022 to First Examination Report dated Jan. 20, 2021", 14 pgs.

"Canadian Application Serial No. 3,088,912, Office Action dated Sep. 17, 2021", 5 pgs.

"Canadian Application Serial No. 3,088,912, Response filed Jan. 17, 2022 to Office Action dated Sep. 17, 2021", 16 pgs.

"Canadian Application Serial No. 3,089,218, Office Action dated Sep. 1, 2021", 3 pgs.

"Canadian Application Serial No. 3,089,218, Response filed Dec. 29, 2021 Office Action dated Sep. 1, 2021", 12 pgs.

"European Application Serial No. 1947526.2, Extended European Search Report dated Oct. 11, 2021", 12 pgs.

"European Application Serial No. 19747760.7, Extended European Search Report dated Oct. 21, 2021", 13 pgs.

Damm, P, et al., "Total hip joint prosthesis for in vivo measurement offerees and moments", Medical Engineering & Physics, Butterworth-Heinemann, GB, vol. 32, No. 1, (Jan. 1, 2010), 95-100.

* cited by examiner

RANGE OF MOTION EVALUATION IN ORTHOPEDIC SURGERY

CLAIM OF PRIORITY

This application is a continuation of U.S. patent application Ser. No. 16/262,482, filed Jan. 30, 2019, now abandoned, which claims the benefit of priority to U.S. Provisional Application Nos. 62/625,706, filed Feb. 2, 2018, titled "SOFT TISSUE BALANCING IN ROBOTIC KNEE SURGERY"; 62/697,227, filed Jul. 12, 2018, titled "SOFT TISSUE BALANCING IN ROBOTIC KNEE SURGERY"; and 62/697,220, filed Jul. 12, 2018, titled "RANGE OF MOTION EVALUATION IN ORTHOPEDIC SURGERY" each of which is hereby incorporated herein by reference in its entirety.

BACKGROUND

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. For example, post-operative range of motion is an important consideration for a surgeon during orthopedic procedures. However, when performing orthopedic surgery on joints, range of motion evaluations are conventionally done by eye, with the surgeon qualitatively assessing the limits of patient's range of motion. The conventional technique may result in errors or lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for using an adjustable spacer in a surgical procedure are provided herein. The systems described herein may include using an adjustable spacer for use during a range of motion test. In an example, the adjustable spacer may be controlled by fixing pressure or fixing distance (e.g., of a neck of a trial for use in an orthopedic procedure, such as on a shoulder or hip) during an evaluation. The adjustable spacer systems and methods described herein may be used with a robotic surgical device.

Robotics offer a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "key-hole" procedures, arthroplasty procedures, such as total or partial knee replacement, hip replacement, shoulder implant procedures, or the like. In an example, a surgical procedure may use a surgical robot. The surgical robot may include a robotic arm for performing operations. A tracking system may be used to determine a relative location of the surgical robot or robotic arm within a coordinate system or a surgical field. The surgical robot may have a different coordinate system or tracking system (e.g., using known movements of the surgical robot). The robotic arm may include an end effector of the robotic arm of the surgical robot, which may use sensors, such as a gyroscope, magnetoscope, accelerometer, etc. In an example, a processor may be used to process information, such as tracking information, operation parameters, applied force, location, or the like.

The systems and methods described herein provide an expandable or adjustable component for use within an orthopedic surgical procedure. For example, a shoulder or hip procedure may include using an adjustable spacer during a range of motion test. The adjustable spacer may include a component inflatable by a pump. The pump may maintain a fixed distance or fixed pressure in the component, for example throughout the range of motion test. Using a fixed distance, a maximum pressure or force may be determined (or various pressures or forces throughout the range of motion). Using a fixed pressure, various distances or a maximum distance may be determined during the range of motion test. The adjustable spacer may be a part of a trial or insert for use in a surgical procedure, for example, a femoral stem or humeral stem may include the adjustable spacer. In another example, a femoral head, humeral head, or glenosphere may include the adjustable spacer. A determined pressure or distance (e.g., maximum throughout a range of motion) may be used to adjust a preoperative plan. For example, a planned implant may be modified to be larger or smaller.

Figure 1:
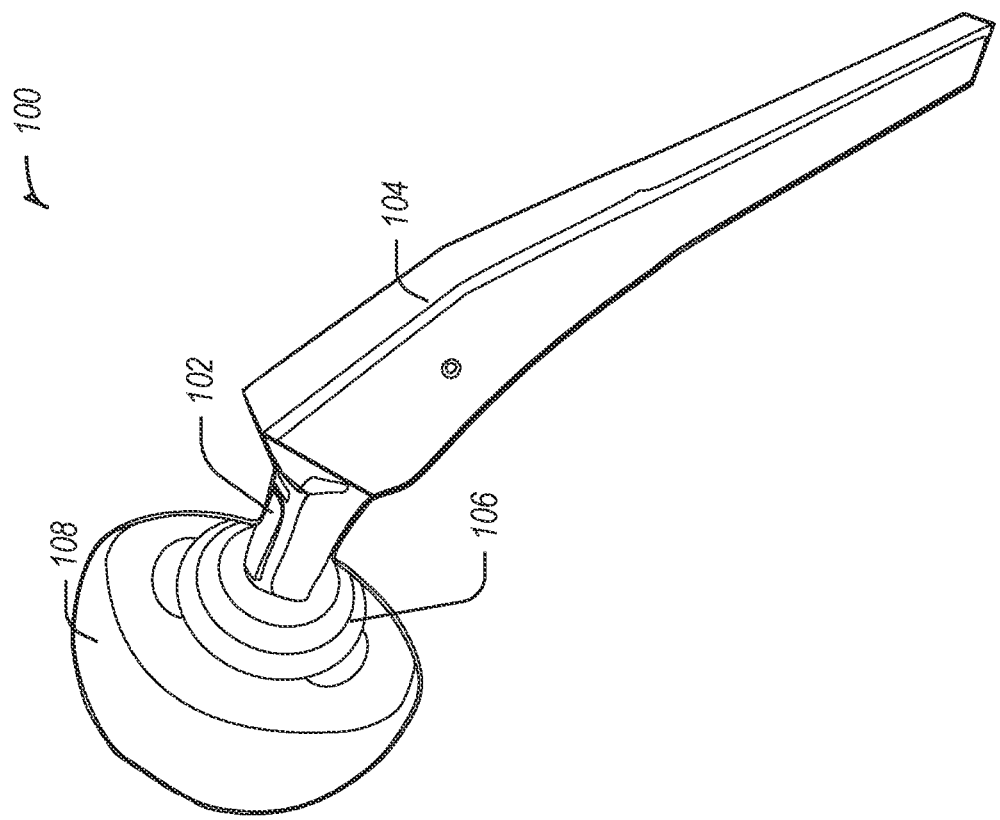
FIG. 1 illustrates an adjustable spacer used in a surgical procedure in accordance with some embodiments.
Figure 1:
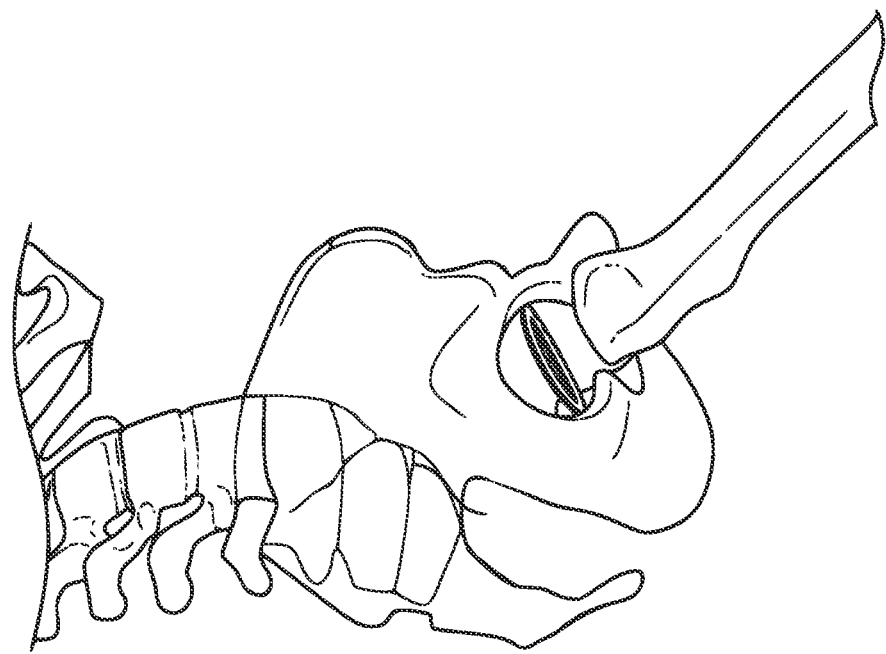

FIG. 1 illustrates an adjustable spacer 102 within a neck component used in a surgical procedure in accordance with some embodiments. The diagram 100 illustrated in FIG. 1 shows the adjustable spacer 102 as part of a hip trial or hip implant, but may also be used with a shoulder trial or a shoulder implant, or for use with other orthopedic surgical trials or implants (e.g., knee). The adjustable spacer 102 may be within a neck component, which may be connected to a shaft 104 and a head 106. The neck therefore may be inflated to change the distance between a proximal end of the shaft 104 and a distal end of the head 106 (defining the distal end of the head 106 to be opposite a proximal end configured to fit into an acetabular component 108, such as a trial). A distal end of the shaft 104 may be embedded into a femur, an acetabulum, or a humerus of a patient (or in the glenoid of the patient in a reverse shoulder arthroplasty procedure).

The neck may experience pressure (e.g., a compression force) from between the head 106 (imparted, for example by the acetabular component 108 onto the head 106) and the shaft 104. In an example, the distance of the neck is controlled to remain equal throughout a range of motion test, while allowing pressure to change. In another example, the pressure in the neck is controlled and held equal throughout a range of motion test while the distance is allowed to change.

The adjustable spacer 102 may be inflated or adjusted using a pump (e.g., which may be controlled by a robotic surgical system in an example). An inflated component of the adjustable spacer 102 may be used during a range of motion test, such as for a hip or shoulder procedure. In an example, a fixed distance or a fixed pressure for the adjustable spacer 102 (e.g., as identified in a surgical plan, which may be a preoperative plan or a plan generated or modified intraoperatively) may be used during the range of motion test. An extrema may be determined, such as a maximum or minimum pressure (for a fixed distance) or maximum or minimum distance (for a fixed pressure) during the range of motion test. The extrema may be output, such as for display on a user interface or for use in automatically adjusting a parameter of a surgical plan. The surgical plan may be modified based on soft tissue tension, a change in implant sizing, or the like, such as based on the extrema.

In an example, an adjustable spacer similar to that described above (102) may be used with a patella. For example, an inflatable trial may be used to replace a patella before a range of motion test is conducted. The inflatable trial may be used at a fixed distance or fixed pressure, and a maximum pressure or maximum distance (respectively) may be determined for the inflatable trial throughout the range of motion. In an example, the inflatable trial may replace the patella and be used after the patella is cut. The range of motion test may be conducted to check stability in the patella with the inflatable trial. In another example, the inflatable trial may be used to place the patella at a new height or distance away from the knee joint, and the range of motion test may use the inflatable trial and the patella together to check stability.

The inflatable trial may be used to check different fixed distances (e.g., away from the knee joint) to determine an optimal fixed distance for range of motion, for example to minimize pressure on the trial. In another example, a fixed pressure may be used in the inflatable trial to determine a range of distances throughout the range of motion (e.g., to determine a maximum distance needed for a fixed pressure). A preoperative plan may be used for any initial testing, and the plan may be automatically adjusted based on results (e.g., changing an initial distance, pressure, or volume).

The surgeon may adjust any planned resections, test, and record the forces (e.g., pressure) captured by a force or pressure sensor throughout a range of motion. This procedure may be repeated as necessary until the plan results in the desired expected tension values. The surgeon may remove bone according to the final plan. Once sufficient bone is removed according to the plan, range of motion may be confirmed with the adjustable spacer 102, or a trial implant.

Figure 2:
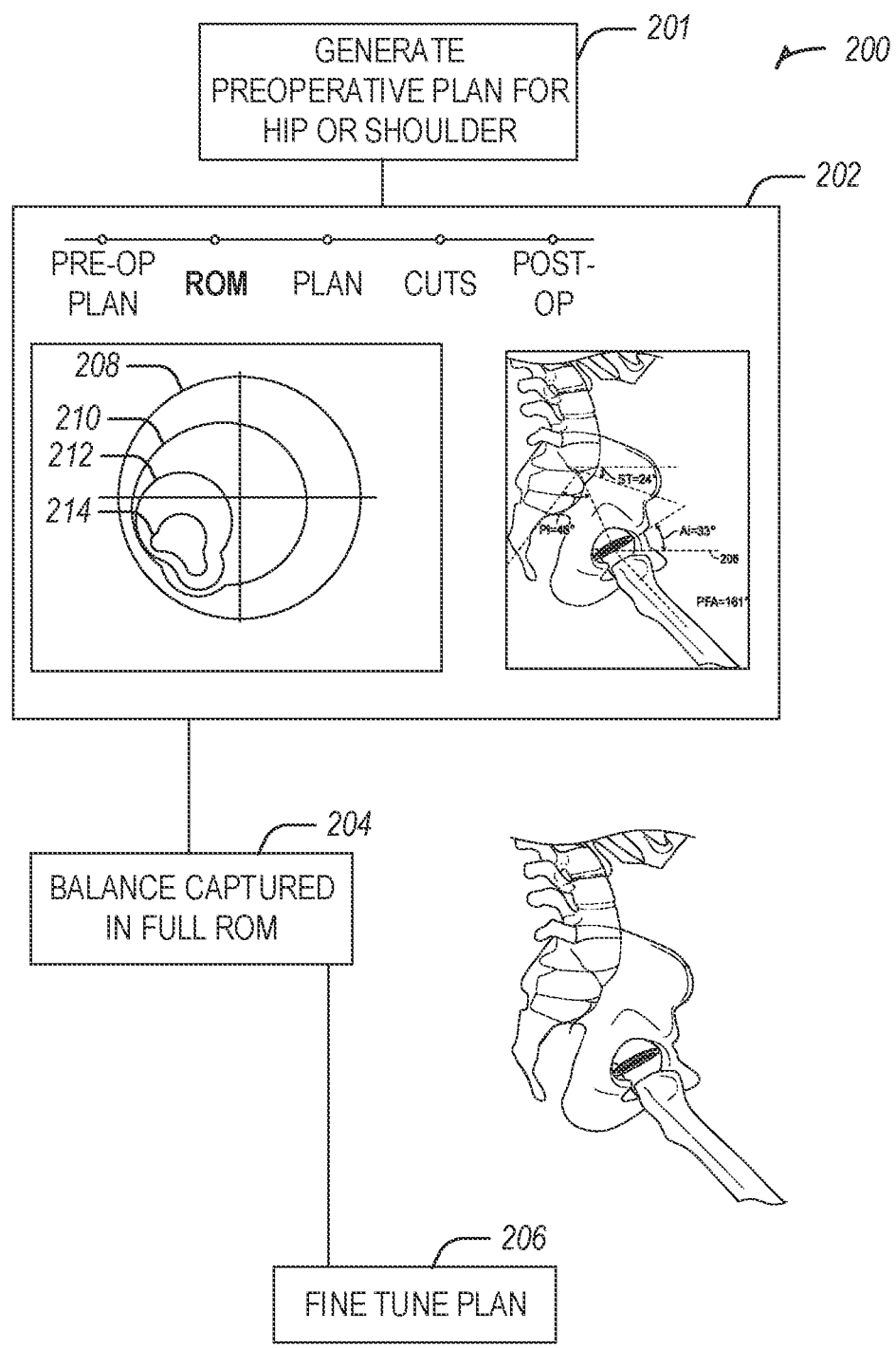
FIG. 2 illustrates a surgical technique in accordance with some embodiments.

FIG. 2 illustrates a surgical technique 200 in accordance with some embodiments. The technique 200 uses an adjustable spacer to perform a range of motion test. The technique 200 includes initiating or generating a plan (e.g., preoperatively) at 201, such as using a user interface 202. The plan may be for an orthopedic procedure, such as for a hip or shoulder.

The user interface 202 may include a visual depiction of a range of motion test. For example, the user interface 202 includes a range of motion visualization component 208. In an example, the range of motion visualization component 208 may be an actual range of motion of a patient, a potential range of motion, an ideal range of motion, a possible range of motion, or a planned range of motion (e.g., after orthopedic surgery). The range of motion may be for a shoulder or hip, in an example. The range of motion visualization component 208 may include one or more zones, such as a green zone 210 representing a pressure or distance for an adjustable spacer within a first tolerance. A yellow zone 212 may represent a pressure or distance between the first tolerance and a second tolerance (e.g., with a potentially problematic pressure or distance). A red zone 214 may represent a pressure or distance beyond the second tolerance (e.g., traversing a planned pressure or distance maximum or minimum). The tolerances or zones may be selected such as preoperatively, in a plan, by a surgeon, etc.

The zones 210-214 may be generated based on the range of motion test (or potential, possible, or ideal range of motion) with a given neck length of an adjustable spacer between a shaft (e.g., femoral shaft) and a cup or head (for a hip procedure). In an example, the range of motion visualization component 208 illustrates a pressure map for three different fixed neck lengths, 210, 212, and 214. The pressure maps may show different pressures at different points around the range of motion for the respective neck lengths.

In another example, a pressure in the adjustable spacer may be fixed and the neck length allowed to change. In this example, the range of motion visualization component 208 illustrates a neck length map for three different fixed pressures, 210, 212, and 214. In this example, the neck lengths change throughout the range of motion for each fixed pressure.

In either of the two above examples (fixed neck length or fixed pressure), a single range of motion test may be run or multiple range of motion tests may be run, such as at different fixed pressures or neck lengths (the three examples are shown for illustration purposes). The resulting map (a pressure map when the neck length is fixed or a neck length map when the pressure is fixed) may be used to change a preoperative plan. For example, a maximum pressure or maximum neck length may be used from the range of motion visualization component 208 to change a planned neck length, implant size, trial size, or the like.

The technique 200 includes an operation 204 to capture balance during a range of motion test, for example using an adjustable spacer. The adjustable spacer is described in more detail below. The technique 200 may include using feedback from the range of motion test to adjust the plan (e.g., automatically change a parameter of the preoperative plan based on the range of motion test, such as balance information, a maximum or minimum distance, range of motion, or implant or trial angle), for example by fine tuning the plan at operation 206. The technique 200 may include performing a resection, burr action, or otherwise reduce bone. The technique 200 may include evaluating balance in soft tissue or for range of motion using the adjustable spacer.

In an example, the technique 200 may include using an optical tracker to track components of a surgery. For example, tracked components may include a leg, an arm, a bone, a tool, or the like. The technique 200 may include performing a range of motion test to evaluate pressure or distance in a shoulder or hip joint over a range. Optical trackers may be used to determine various attributes of bones or soft tissue during the range of motion test. For example, distance traveled by the leg or arm throughout the range of motion test, angle of bone during the range of motion test (e.g., a maximum angle), distance at various points or throughout the range of motion test, or the like.

In an example, the distance or pressure may be shown on a user interface during the range of motion test. The distance may be shown based on a planned bone removal (or a resection). The planned bone removal may be shown on the user interface, along with distance or pressure throughout the range of motion test to display differences or issues that may arise based on the planned bone removal and the evaluated pressure or distance.

The technique 200 may include establishing the preoperative plan and showing the hip or shoulder with the planned resections on the user interface. Then as distance or pressure are determined throughout the range of motion test, the distance or pressure are displayed on the user interface with the planned bone removal. This combination of pre-planned bone removal visualization with actual measured distance or pressure information allows for evaluation of the planned bone removal with real feedback. This combination also allows for evaluating the ultimate distance or pressure with the planned bone removal rather than distance or pressure pre-bone removal, which may not ultimately be accurate. The combination further allows for accurate planning of what the soft tissue balancing (e.g., rotation of the leg or arm relative to the hip or shoulder joint, respectively) will be after the planned bone removal without needing to actually perform the bone removal. This allows for accurate planning, and modification to the bone removal may be made.

In an example the technique 200 may include displaying the measured and actual neck distance or pressure with the planned bone removal by reference to a hip or shoulder, and an axis or a plane of a bone (e.g., a femoral axis). The distance or pressure may be measured using a sensor on an adjustable spacer as described throughout this disclosure.

In an example, the range of motion test may include registering the femur with reference to a bone model (e.g., a preoperative plan), and registering a tracker for the femur (the humerus or glenoid may be registered and tracked for a shoulder procedure). The range of motion test is then performed. The femur, the glenoid, or the humerus is tracked throughout the range of motion test. The distance or pressure at a point or throughout a range (e.g., a maximum distance or pressure, an animation of distance or pressure throughout the range of motion, or a distance or pressure at a selectable angle of range of motion) may be displayed on the user interface.

Figure 3:
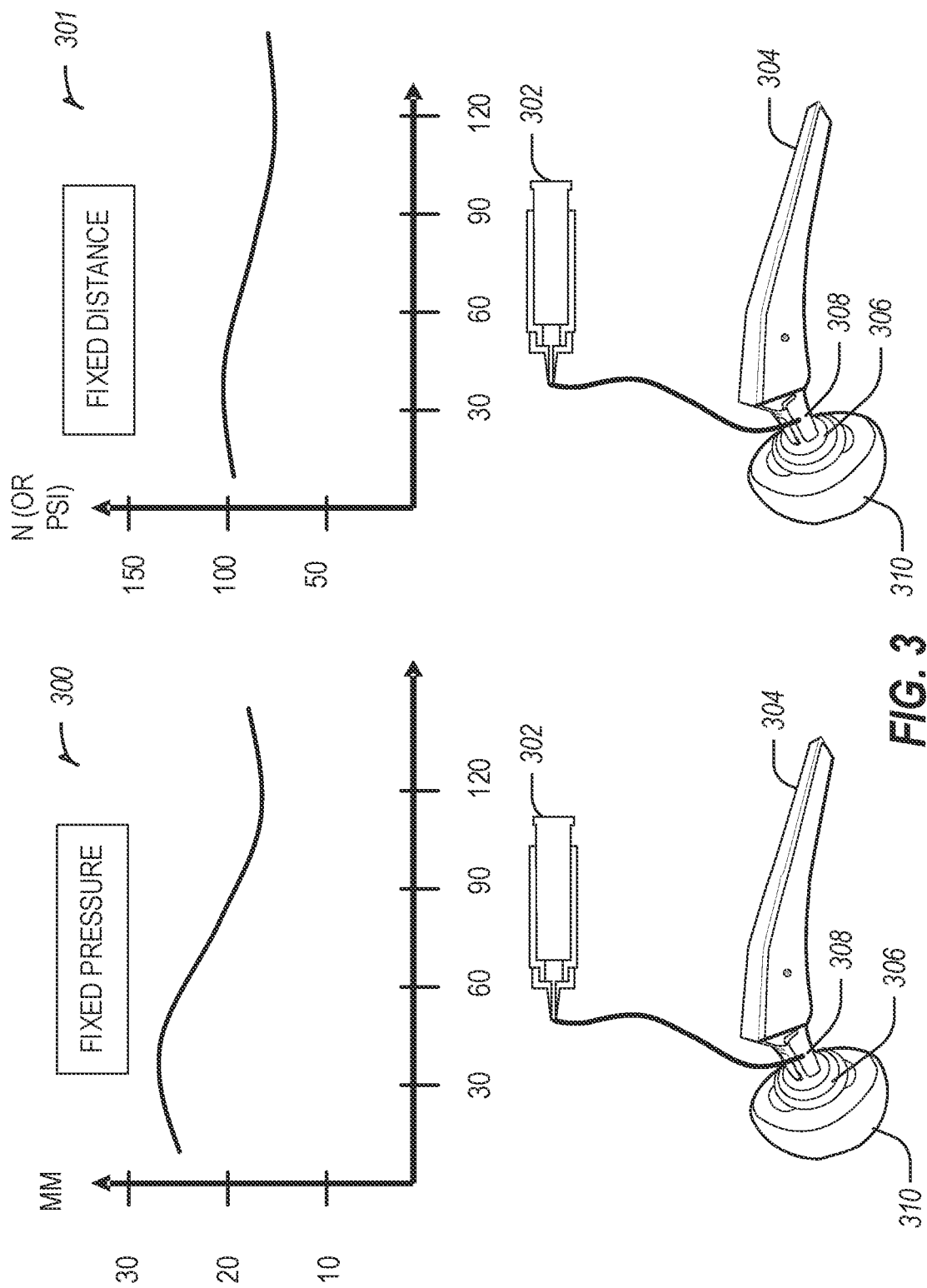
FIG. 3 illustrates an adjustable spacer and graphs showing effects of the adjustable spacer in accordance with some embodiments.

FIG. 3 illustrates an adjustable spacer and graphs 300 and 301 showing effects of the adjustable spacer in accordance with some embodiments. The adjustable spacer may be used within a hip or shoulder, such as for a surgical procedure. The adjustable spacer may be used to measure, determine, or change a distance or pressure difference within a neck 308 of a trial or implant for use with a femur, an acetabulum, a glenoid, or a humerus of a patient. For example, the adjustable spacer may be placed into the neck 308 between a head 306 and a shaft 308 to be inserted into the femur, the acetabulum, the glenoid, or the humerus. The adjustable spacer may be inflated to measure distance or pressure, for example throughout a range of motion test. The head 306 may fit into an acetabular component 310 (e.g., trial), as adjusted by the neck 308.

In the illustrated femoral stem/head prosthesis, the adjustable spacer operates to shift the position of the femoral head portion 306 to extend or contract the neck 308 of the femoral stem. Adjusting the neck length (e.g., by extending or shortening the neck 308) may be an adjustment to a preoperative plan, for example based on a maximum pressure or distance determined during a range of motion test. In another example, the adjustable spacer may be located within the femoral head portion 306, and be used to determine an adjustment to the head size of the femoral head (e.g., from a preoperative plan).

The adjustable spacer is shown in a first controlled configuration corresponding to graph 300 and a second controlled configuration corresponding to graph 301. The first configuration includes controlling the adjustable spacer such that the pressure within the adjustable spacer is fixed. A fixed pressure means that the pressure output from a pump or pumps is maintained within the adjustable spacer while distance (e.g., length or volume of the spacer) is allowed to fluctuate (e.g., during a range of motion test).

Graph 300 illustrates changes in distance for the fixed pressure adjustable spacer throughout a range of motion test. Graph 300 has an x-axis illustrating degrees of the range of motion test. The y-axis of graph 300 illustrates a distance (e.g., in the example shown in FIG. 3, fluctuating between 0 and 30 mm). The graph 300 may be output to a user interface on a display (e.g., a display of a robotic surgical system) for evaluation by a surgeon. In an example, a maximum or minimum distance for the adjustable spacer may be determined from the range of motion test. The maximum or minimum distance may be used to adjust a surgical plan (e.g., a preoperative plan), such as by changing a parameter for a planned bone removal, changing an implant size, or adjusting soft tissue (e.g., releases). The changes to the preoperative plan may be made automatically, for example changing a parameter of a planned bone removal by a robotic arm. In an example, a change may include determining a longer or shorter neck length for a trial or implant or changing a cup size or cup position (of a trial or implant acetabular cup). For example, a user interface may be used to provide a length needed of implant neck to achieve the tested pressure (e.g., a maximum pressure).

The second configuration includes controlling the adjustable spacer such that the distance is fixed. A fixed distance means that the pressure output from a pump or pumps varies throughout a range of motion test for the adjustable spacer. The adjustable spacer is thus fixed to a certain distance, which may be determined as part of a preoperative plan or interoperative change to a preoperative plan. The change in pressure may be adjusted during a range of motion test to retain the fixed distance. The change in pressure may correspond to a change in force (e.g., 35 N for 7 psi and 52 N for 12 psi).

Graph 301 illustrates changes in pressure for the fixed distance in the adjustable spacer throughout a range of motion test. Graph 301 has an x-axis illustrating degrees of the range of motion test. The y-axis of graph 301 may illustrate a pressure (e.g., applied from a pump) or a force applied by the or within the adjustable spacer (e.g., in the example shown in FIG. 3, a force is illustrated). The graph 301 may be output to a user interface on a display (e.g., a display of a robotic surgical system) for evaluation by a surgeon. In an example, a maximum or minimum pressure for the adjustable spacer may be determined from the range of motion test. The maximum or minimum pressure may be used to adjust a surgical plan (e.g., a preoperative plan), such as by changing a parameter for a planned bone removal of the femur, the acetabulum, the glenoid, or the humerus, changing an implant size, or adjusting soft tissue (e.g., releases). The changes to the preoperative plan may be made automatically, for example changing a parameter of a planned resection by a robotic arm. In an example, a change may include determining a longer or shorter neck length for a trial or implant. For example, a user interface may be used to provide a length needed of implant neck to achieve the tested pressure (e.g., a maximum pressure).

Figure 4:
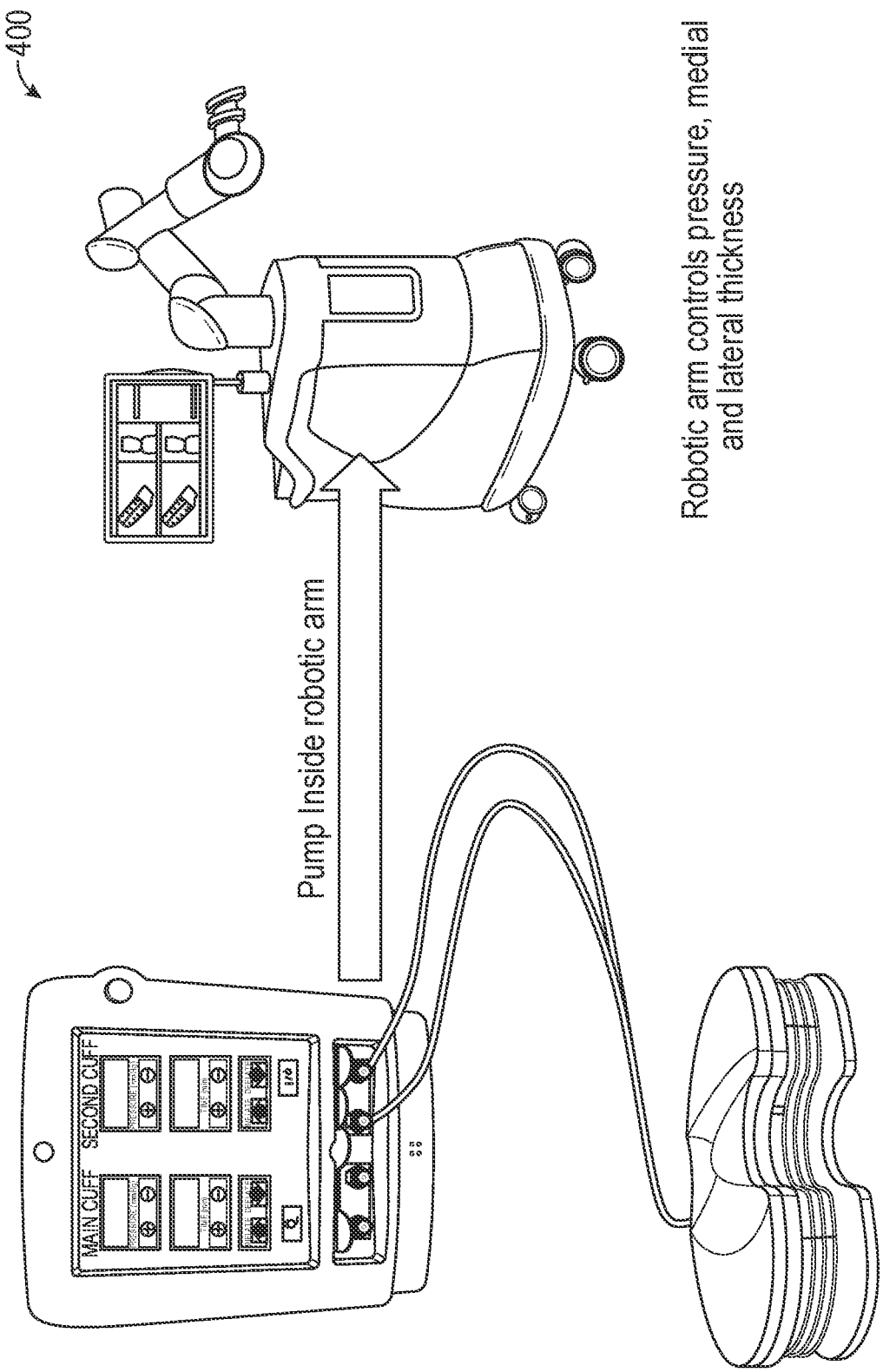
FIG. 4 illustrates a system for using an adjustable spacer with a robotic surgical device in accordance with some embodiments.

FIG. 4 illustrates a system 400 for using an adjustable spacer with a robotic surgical device in accordance with some embodiments. The system 400 may include a robotic surgical system or device (e.g., a Rosa), which may include a user interface and a robotic arm. The robotic surgical system or device may include a pump, be configured to hold or support a pump, interface with a pump, or the like. In another example, the system 400 may include a pump separate from the robotic surgical system or device. The pump (which may include more than one pump) may be used to control an adjustable spacer. In the example where the pump is controlled by the robotic system or device, a processor of the robotic system or device may control pressure output to one or more components of the adjustable spacer. The robotic surgical system or device may be used to control the pump during a range of motion test, such as to evaluate distance or pressure in the adjustable spacer (e.g., during a hip or shoulder procedure).

Figure 5:
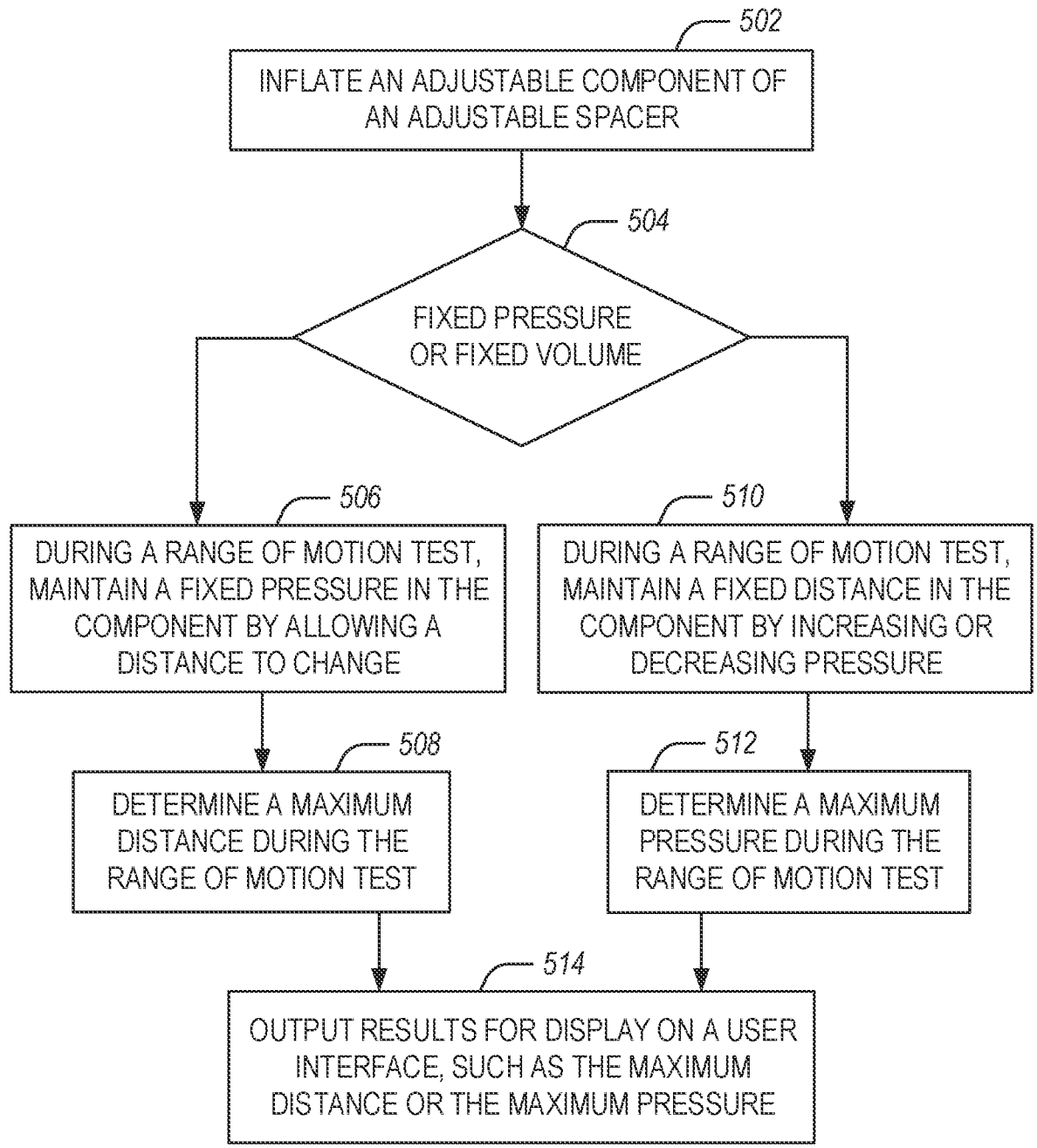
FIG. 5 illustrates a flowchart showing a technique for using an adjustable spacer in a surgical knee procedure in accordance with some embodiments.

FIG. 5 illustrates a flowchart showing a technique 500 for using an adjustable spacer in a surgical procedure, such as a shoulder or hip procedure, in accordance with some embodiments. The technique 500 includes an operation 502 to inflate (e.g., using a pump) an adjustable component of an adjustable spacer (e.g., of an implant or a trial). The technique 500 includes a decision operation 504 to determine whether a fixed pressure or a fixed distance (or volume) is to be used for a range of motion test.

The technique 500 includes an operation 506 to, during a range of motion test, maintain a fixed pressure in the component by allowing a distance (e.g., of a neck in a trial for a hip or shoulder implant) to change. The technique 500 includes an operation 508 to determine a maximum distance during the range of motion test. The technique 500 includes an operation 510 to, during a range of motion test, maintain a fixed distance in the component by increasing or decreasing pressure (e.g., using a pump). The technique 500 includes an operation 512 to determine a maximum pressure during the range of motion test.

In an example, the fixed distance or the fixed pressure may be determined using a preoperative plan. The preoperative plan may be adjusted based on the maximum distance or the maximum pressure determined during the range of motion test. In an example, an implant or a trial may be determined using the maximum distance or the maximum pressure. The maximum pressure or the maximum distance may be determined using a sensor (e.g., an iAssist device) or an optical tracker. In an example, a change to a preoperative plan may include determining a longer or shorter neck length for a trial or implant. For example, a user interface may be used to provide a length needed of implant neck to achieve the tested pressure (e.g., a maximum pressure).

The technique 500 includes an operation 514 to output results for display on a user interface, such as the maximum distance or the maximum pressure determined during the range of motion test. In an example, operations 506-508 may be done independently from operations 510-512, such as only doing one set of operations, or doing each set sequentially (e.g., fixed pressure range of motion test then fixed distance range of motion test, or vice versa). In an example, the fixed distance or the fixed pressure may be increased or decreased during a repeated range of motion test.

In an example, a surgical device used to operate the pump is a robotic surgical device, and a processor may operate a robotic controller. In this example, the pump is controlled by the processor, and the robotic surgical device includes a display, the display configured to present the user interface including the maximum pressure or the maximum distance.

In an example, the pressure and the gap distance may be allowed to change during the range of motion test. In this example, a 3D plan (e.g., a preoperative plan) may be used to set limits or targets for gap distance or pressure. For example, a maximum pressure may be set for different angles (e.g., from extension to flexion) or a maximum distance may be set. The technique 500 may then proceed to, during a range of motion test, maintain a neck distance or pressure based on the 3D plan. At some portions of the range of motion test, the neck distance may be held constant while at other portions of the range of motion test, the pressure may be held constant, according to the 3D plan. The technique 500 may include an operation to determine a maximum pressure or maximum neck distance during the range of motion test (e.g., at different portions of the test, based on when the neck distance or the pressure is held constant, respectively).

Figure 6:
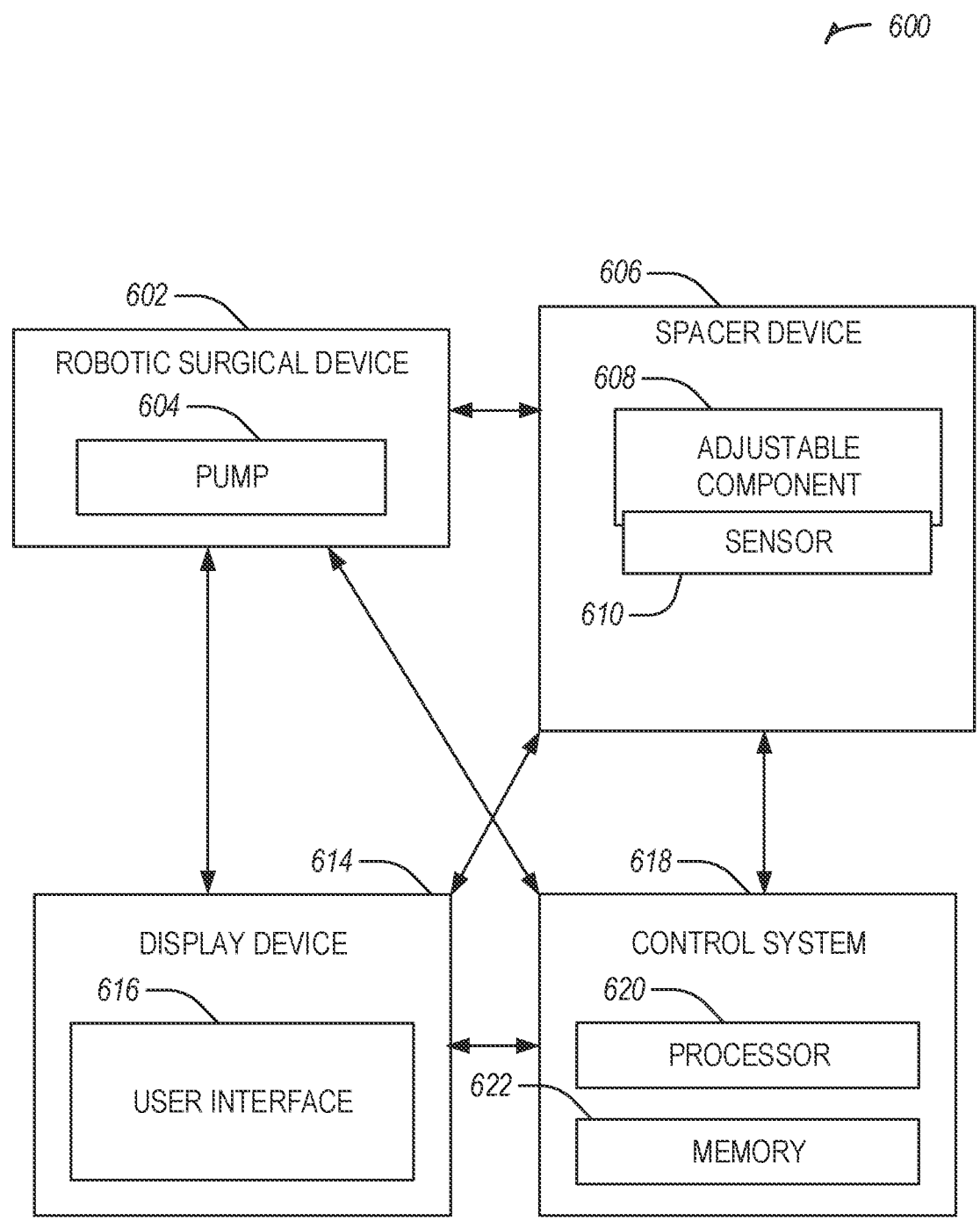
FIG. 6 illustrates a system for performing techniques described herein, in accordance with some embodiments.

FIG. 6 illustrates a system 600 for performing techniques described herein, in accordance with some embodiments. The system 600 includes a robotic surgical device 602, which may be coupled to a pump 604 (in an example not shown, pump 604 is a stand-alone pump, not coupled to a robotic device), which may be used to control a spacer device 606 (e.g., an implant or a trial). The spacer device 606 includes an adjustable component 608. The system 600 may include a display device 614, which may be used to display a user interface 616. The system 600 may include a control system 618 (e.g., a robotic controller), including a processor 620 and memory 622. In an example, the display device 614 may be coupled to one or more of the robotic surgical device 602, the spacer device 606, or the control system 618.

In an example, the display device 614 may be used to display results of a range of motion procedure on the user interface 616. The results may include distance or pressure information, such as over different angles during a range of motion test. The distance or pressure information may be derived from a sensor, such as a sensor 610, which may be on the adjustable component 608 or elsewhere on or within the spacer device 606. The sensor 610 may be a Hall effect sensor. The distance or pressure information may be related to a shoulder or hip joint.

Figure 7:
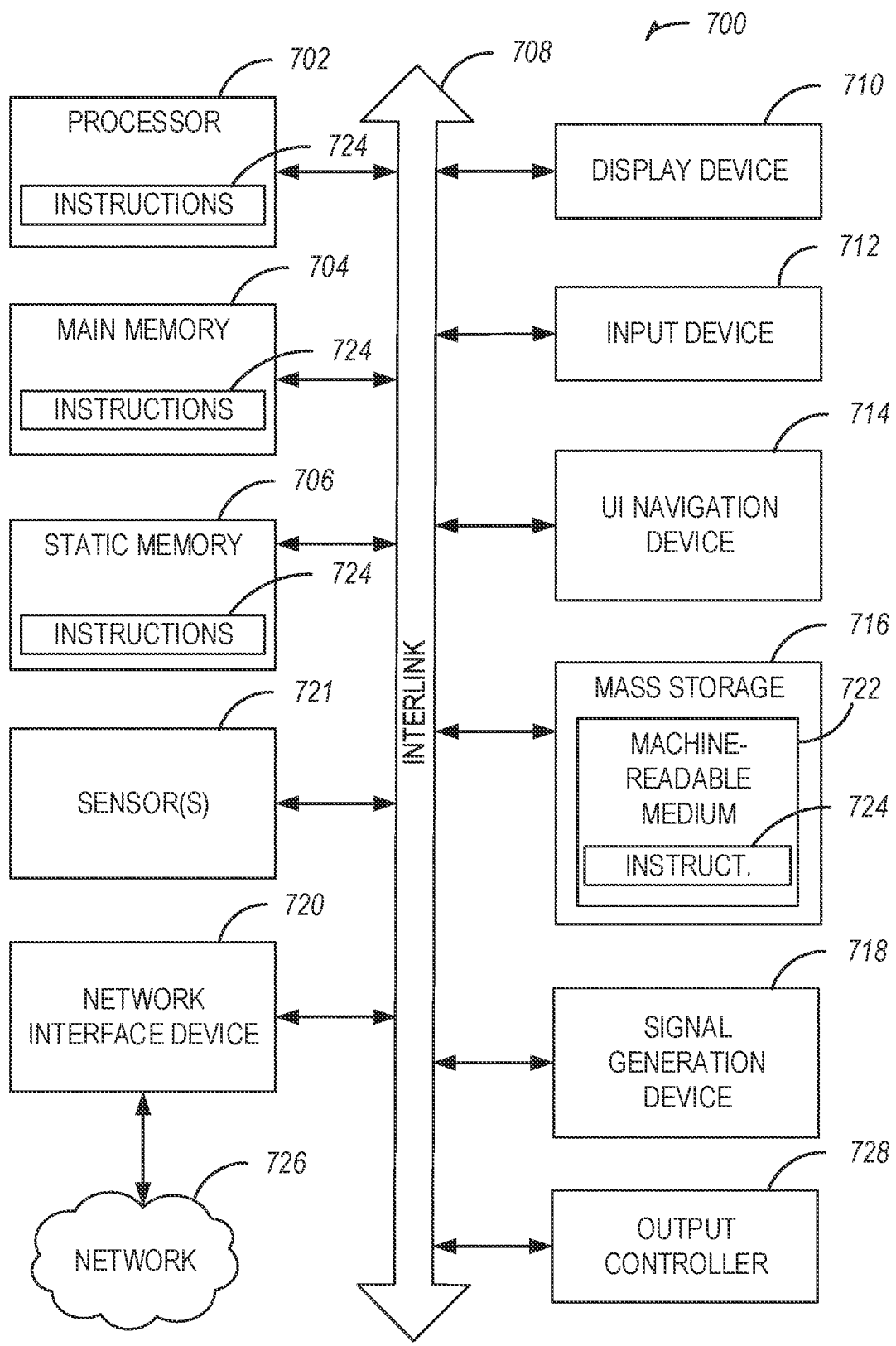
FIG. 7 illustrates a block diagram of an example of a machine upon which any one or more of the techniques discussed herein may perform in accordance with some embodiments.

FIG. 7 illustrates a block diagram of an example machine 700 upon which any one or more of the techniques discussed herein may perform in accordance with some embodiments. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724. The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®, IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Each of these non-limiting examples may stand on its own, or may be combined in various permutations or combinations with one or more of the other examples.

Example 1 is a surgical device for evaluating soft tissue during a surgical procedure comprising: a pump to: inflate an adjustable spacer in a neck portion of a femoral trial for a hip replacement procedure; and during a range of motion test, maintain a fixed distance in the adjustable spacer by increasing or decreasing pressure in the adjustable spacer; and a processor to: determine a maximum pressure during the range of motion test; and output the maximum pressure for display on a user interface.

In Example 2, the subject matter of Example 1 includes, wherein the pump is further to decrease the fixed distance during a repeated range of motion test.

In Example 3, the subject matter of Examples 1-2 includes, wherein the processor is to use a preoperative plan to determine the fixed distance.

In Example 4, the subject matter of Example 3 includes, wherein the processor is further to adjust the preoperative plan based on the maximum pressure.

In Example 5, the subject matter of Examples 1-4 includes, wherein the processor is further to determine an implant based on the maximum pressure.

In Example 6, the subject matter of Examples 1-5 includes, wherein to determine the maximum pressure, the processor is to use optical tracking of the neck portion of the femoral trial.

In Example 7, the subject matter of Examples 1-6 includes, wherein the surgical device is a robotic surgical device, wherein the processor operates a robotic controller, wherein the pump is controlled by the processor, and wherein the robotic surgical device includes a display, the display configured to present the user interface including the maximum pressure.

Example 8 is a method comprising: inserting a trial for a hip replacement procedure, the trial including an adjustable spacer in a neck portion; inflating the adjustable spacer to a fixed distance; using a pressure sensor device, measuring pressure on the adjustable spacer throughout a range of motion test with the trial in place and the adjustable spacer inflated at the fixed distance; determining a maximum pressure during the range of motion test; and outputting the maximum pressure for display on a user interface.

In Example 9, the subject matter of Example 8 includes, decreasing the fixed distance and performing the range of motion test again.

In Example 10, the subject matter of Examples 8-9 includes, using a preoperative plan to determine the fixed distance.

In Example 11, the subject matter of Example 10 includes, adjusting the preoperative plan based on the maximum pressure.

In Example 12, the subject matter of Examples 8-11 includes, determining an implant based on the maximum pressure.

In Example 13, the subject matter of Examples 8-12 includes, determining the maximum pressure using an iAssist device.

Example 14 is a machine-readable medium including instructions for controlling an adjustable spacer of a trial inserted into a femur of a patient for a hip replacement procedure, which when executed by a processor, cause the processor to: cause the adjustable spacer to inflate to a fixed distance; receive pressure measurements from a pressure sensor device, the pressure measurements taken by the pressure sensor device on the adjustable spacer throughout a range of motion test with the trial in place and the adjustable spacer inflated at the fixed distance; determine a maximum pressure during the range of motion test; and output the maximum pressure for display on a user interface.

In Example 15, the subject matter of Example 14 includes, wherein the instructions further cause the processor to cause the fixed distance of the adjustable spacer to decrease, during a repeat of the range of motion test.

In Example 16, the subject matter of Examples 14-15 includes, wherein the processor is further to use a preoperative plan to determine the fixed distance.

In Example 17, the subject matter of Example 16 includes, wherein the processor is further to adjust the preoperative plan based on the maximum pressure.

In Example 18, the subject matter of Examples 14-17 includes, wherein the processor is further to determine an implant based on the maximum pressure.

In Example 19, the subject matter of Examples 14-18 includes, wherein the processor is to receive the pressure measurements from an iAssist device.

Example 20 is at least one machine-readable medium including instructions that, when executed by processing circuitry, cause the processing circuitry to perform operations to implement of any of Examples 1-19.

Example 21 is an apparatus comprising means to implement of any of Examples 1-19.

Example 22 is a system to implement of any of Examples 1-19.

Example 23 is a method to implement of any of Examples 1-19.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method, comprising:
   generating a preoperative plan for a robotically-assisted hip arthroplasty;
   providing a robotic surgical system having one or more integral pumps;
   performing robotically-assisted burring of a patient's hip joint;
   inserting a trial in a proximal femur of the hip joint during a hip replacement procedure, the trial including an adjustable spacer in a neck portion;
   inflating the adjustable spacer to a fixed neck length;
   measuring force on the adjustable spacer throughout a range of motion test of the hip joint using a force sensor device, with the trial in place and the adjustable spacer inflated at the fixed neck length;
   tracking a position of bones of the hip joint utilizing an optical tracking system operatively coupled to the robotic surgical system throughout the range of motion test;
   determining a maximum force measured by the force sensor device during the range of motion test;
   outputting the maximum force for display on a user interface coupled to the robotic surgical system; and
   changing a planned femoral implant size of the preoperative plan based on the maximum force.

2. The method of claim 1, further comprising decreasing the fixed neck length and performing the range of motion test again.

3. The method of claim 1, further comprising displaying the position of the bones during the range of motion test on the display.

4. The method of claim 1, further comprising changing a parameter of a planned bone removal by the robotic surgical system based on the maximum force.

5. The method of claim 1, further comprising changing at least one of a cup size or a cup position of an implant acetabular cup based on the maximum force.

6. The method of claim 1, wherein inflating the adjustable spacer to the fixed neck length includes maintaining the adjustable spacer at the fixed neck length throughout the range of motion test by using at least one of the one or more integral pumps of the robotic surgical system to control pressure within the neck portion of the trial.

7. The method of claim 6, wherein the at least one of the one or more integral pumps is controlled by a processor of the robotic surgical system.

8. The method of claim 1, wherein outputting the maximum force for display on the user interface includes displaying a graph showing measured force over time throughout the range of motion test.

9. The method of claim 1, further comprising displaying, on the user interface, an indication that a measured force during the range of motion test exceeded a threshold.

10. A method, comprising:
    generating a preoperative plan for the robotically-assisted hip arthroplasty;
    providing a robotic surgical system having one or more integral pumps;
    performing robotically-assisted burring of a patient's hip joint;
    inserting a trial in a proximal femur of the hip joint during a hip replacement procedure, the trial including an adjustable spacer in a neck portion;
    inflating the adjustable spacer to a fixed pressure;
    measuring neck length on the adjustable spacer throughout a range of motion test of the hip joint using a sensor device, with the trial in place and the adjustable spacer inflated at the fixed pressure;
    tracking a position of bones of the hip joint utilizing an optical tracking system operatively coupled to the robotic surgical system throughout the range of motion test;

determining a maximum neck length measured by the force sensor device during the range of motion test;

outputting the maximum neck length for display on a user interface coupled to the robotic surgical system, and;

changing a planned femoral implant size of the preoperative plan based on the maximum neck length.

11. The method of claim 10, further comprising decreasing the fixed pressure and performing the range of motion test again.

12. The method of claim 10, further comprising displaying the position of the bones during the range of motion test on the display.

13. The method of claim 10, further comprising changing a parameter of a planned bone removal by the robotic surgical system based on the maximum neck length.

14. The method of claim 10, further comprising changing at least one of a cup size or a cup position of an implant acetabular cup based on the maximum neck length.

15. The method of claim 10, wherein inflating the adjustable spacer to the fixed pressure includes maintaining the adjustable spacer at the fixed pressure throughout the range of motion test by using at least one of the one or more integral pumps of the robotic surgical system to control pressure within the neck portion of the trial.

16. The method of claim 15, wherein the at least one of the one or more integral pumps is controlled by a processor of the robotic surgical system.

17. The method of claim 10, wherein outputting the maximum neck length for display on the user interface includes displaying a graph showing measured neck length over time throughout the range of motion test.

18. The method of claim 10, further comprising displaying, on the user interface, an indication that a measured neck length during the range of motion test traversed a threshold.

* * * * *